United States Patent [19]

Matsen, III et al.

[11] Patent Number: 5,032,132
[45] Date of Patent: Jul. 16, 1991

[54] GLENOID COMPONENT

[75] Inventors: Frederick A. Matsen, III, Seattle, Wash.; John A. Engelhardt, Warsaw, Ind.

[73] Assignee: Boehringer Mannheim Corporation, Indianapolis, Ind.

[21] Appl. No.: 468,267

[22] Filed: Jan. 22, 1990

[51] Int. Cl.$^5$ .............................................. A61F 2/40
[52] U.S. Cl. ...................................... 623/19; 623/18; 623/20; 623/21
[58] Field of Search ........................ 623/18, 19, 20, 21

[56] References Cited

U.S. PATENT DOCUMENTS

| | | | |
|---|---|---|---|
| 3,803,641 | 4/1974 | Golyakhovsky | 623/19 |
| 4,042,980 | 8/1977 | Swanson et al. | 623/19 |
| 4,045,825 | 9/1977 | Stroot | 623/19 |
| 4,045,826 | 9/1977 | Stroot | 623/19 |
| 4,206,517 | 6/1980 | Pappas et al. | 623/18 |
| 4,355,429 | 10/1982 | Mittelmeier et al. | 623/20 |
| 4,865,605 | 9/1989 | Dines et al. | 623/19 |

FOREIGN PATENT DOCUMENTS 2041929 10/1980 Fed. Rep. of Germany ........ 623/19
2418644 11/1979 France .................................. 623/19

OTHER PUBLICATIONS

"The Cofield Total Shoulder System", 1989, by Richards Medical Company.

Primary Examiner—Randall L. Green
Assistant Examiner—Stephanie L. Iantorno
Attorney, Agent, or Firm—Barnes & Thornburg

[57] ABSTRACT

A prosthetic glenoid component is provided for attachment to a glenoid surface of a scapula to replace a natural socket of a shoulder. The glenoid component includes a molded plastic body having an outer concave bearing surface for engagement by a corresponding humeral head and an inner convex surface for abutting the glenoid surface. A plurality of attachment pegs are integrally molded on the inner surface of the glenoid component for penetrating the glenoid surface to secure the plastic body to the glenoid surface.

34 Claims, 1 Drawing Sheet

GLENOID COMPONENT

BACKGROUND AND SUMMARY OF THE INVENTION

The present invention relates to a prosthetic glenoid component for attachment to a glenoid surface of a scapula to replace a natural socket of a shoulder and to provide a bearing surface for a head portion of an arm bone or humerus. More particularly, the present invention relates to a polymeric glenoid component including a body portion having integrally formed attachment legs extending away from the body portion for penetrating the glenoid surface to secure the body portion to the glenoid surface.

The glenoid component of the present invention is designed for use in a total shoulder replacement procedure. In a total shoulder replacement procedure, a humeral component having a head portion is used to replace the natural head portion of the humerus. The humeral component typically has an elongated intramedullary stem to secure the humeral component to the humerus. The glenoid portion of the scapula is resurfaced with a glenoid component which provides a bearing surface for the head portion of the humeral component.

It is known in the prior art to provide glenoid components for replacing a glenoid surface which include plastic inserts coupled to metal trays or backings. The metal backings are used to secure the plastic inserts to the glenoid surface. The backings are typically made from titanium or other suitable metals. The metal backings are typically attached to the glenoid surface using metal fixation screws. An example of a prior art glenoid component using this two-piece glenoid component construction is shown in U.S. Pat. No. 4,865,605.

Several problems arise from the use of two-piece glenoid components. One problem is the possibility of separation of the plastic insert from the metal backing. If such separation occurs, the glenoid component must be replaced. Another problem is that wear of the plastic insert inherently occurs at the interface between the plastic insert and the metal backing. Over time, this wear can cause failure of the glenoid component. Also, the increased thickness required by the metal backing undesirably increases the height of the replacement glenoid surface which can result in stretching and tightening of the soft tissue associated with the shoulder joint.

One object of the present invention is to provide a suitable one-piece glenoid component to eliminate the need for a two-piece glenoid component.

Another object of the present invention is to stabilize the glenoid component to prevent movement of the glenoid component after the glenoid component is attached to the glenoid surface.

Yet another object of the present invention is to provide a glenoid component having integrally formed attachment pegs to facilitate attachment of the component to the glenoid surface.

Still another object of the present invention is to strengthen the bond between the glenoid component and the bone to reduce the likelihood that the glenoid component will become loose after attachment to the glenoid surface.

A further object of the present invention is to provide a thin replacement glenoid surface which does not significantly alter the height of the natural glenoid surface.

According to the present invention, a glenoid component is provided for attachment to a glenoid surface of a scapula to provide a bearing surface for a head portion of a humerus. The glenoid component includes a body portion having a first surface for abutting the glenoid surface and a second surface for providing the bearing surface for the head portion. The glenoid component includes a plurality of attachment legs extending away from the first surface of the body portion for penetrating the glenoid surface to secure the body portion to the glenoid surface. The plurality of attachment pegs are aligned with respect to each other to lie in a single plane. The glenoid component includes stabilizing means located on the body portion to engage the glenoid surface to prevent movement of the body portion for stabilizing the body portion when the body portion is attached to the glenoid surface.

In a preferred embodiment of the present invention, the stabilizing means includes first and second stabilizing pegs extending away from the first surface of the body portion for penetrating the glenoid surface to prevent movement of the body portion when the body portion is attached to the glenoid surface. The first and second stabilizing pegs are spaced apart in opposite directions from the attachment peg plane and are aligned with respect to each other to lie in a plane normal to the attachment peg plane.

The attachment pegs and stabilizing pegs are designed to be inserted into a plurality of holes formed in the glenoid surface by a suitable drilling tool. A drill guide may be used to properly align the holes in the glenoid surface. The attachment pegs and stabilizing pegs are secured within the holes drilled into the glenoid surface with bone cement.

Selected ones of the plurality of attachment pegs are formed to include a plurality of serrations for receiving a portion of the bone cement to secure the selected attachment pegs within the holes drilled into the glenoid surface. The stabilizing pegs are also formed to include a plurality of serrations for receiving a portion of the bone cement to secure the stabilizing pegs within the holes drilled into the glenoid surface. The serrations cooperate with the bone cement to increase the strength of the bond between the attachment pegs and the bone.

One feature of the present invention is the provision of a one-piece glenoid component having a body portion including a convex surface which matches the shape of and abuts the glenoid surface and a generally concave surface for providing a bearing surface for a head portion of the humerus. The body portion is integrally formed with a plurality of attachment pegs extending away from the convex surface for securing the body portion to the glenoid surface. The integral configuration of the glenoid component of the present invention eliminates the problem of wear between the plastic insert and the metal backing found in prior art glenoid components. This configuration also eliminates the risk of separation of the plastic insert from the metal backing after installation which is also present in prior art glenoid components. Therefore, the present invention advantageously eliminates the need for a two-piece glenoid component. Because only a single integral component is provided, the glenoid component of the present invention is easier to install than conventional glenoid components and provides a thinner replacement surface which does not significantly alter the natural height of the glenoid surface to prevent undesired soft tissue stretching and tightening.

Another feature of the present invention is the provision of stabilizing pegs extending away from the first surface of the glenoid component. The stabilizing pegs penetrate the glenoid surface to prevent movement of the body portion of the glenoid component when the body portion is attached to the glenoid surface. By positioning the stabilizing pegs in a spaced apart relation from the attachment pegs, the stabilizing pegs advantageously prevent movement of the glenoid component and provide stability to the glenoid component when the component is attached to the glenoid surface. The stabilizing pegs prevent rocking movement of the glenoid component when the humeral head engages the bearing surface of the glenoid component. Additionally, matching the shape of the convex surface with the shape of the natural glenoid surface also acts to increase the stability of the implanted component.

Yet another feature of the present invention is the provision of integrally formed attachment pegs extending away from the body portion of the glenoid component which are formed to include a plurality of notches or serrations for receiving a portion of the bone cement to secure the attachment pegs within the holes drilled into the glenoid surface. Bone cement enters the serrations to increase the contact area between the bone cement and the attachment pegs. This feature advantageously strengthens the bond between the attachment pegs and the bone.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
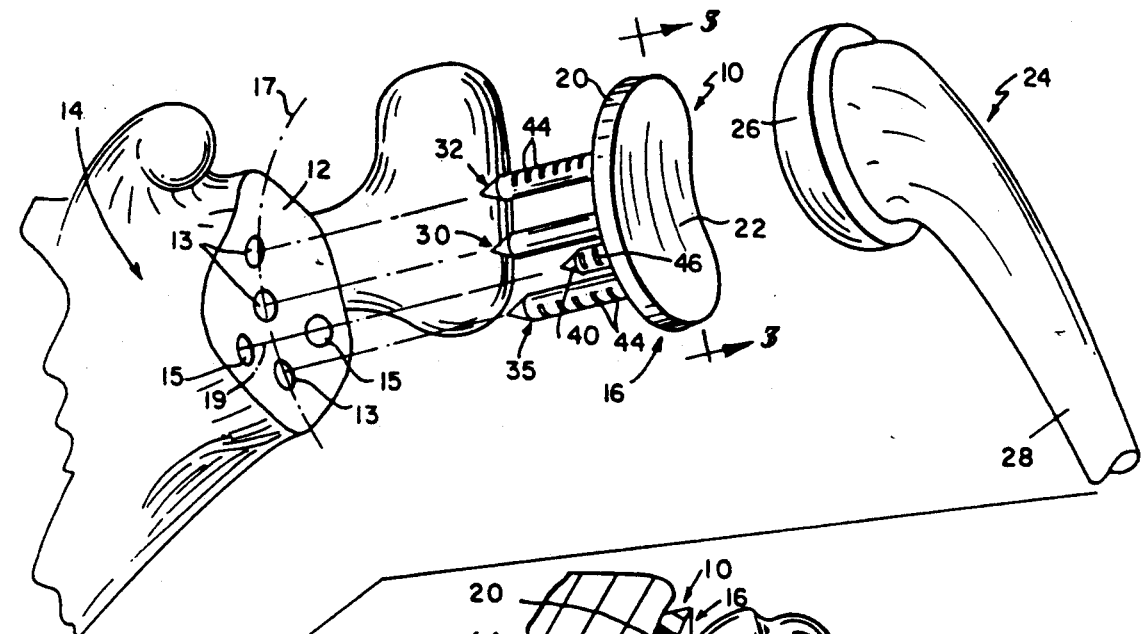
FIG. 1 is an exploded perspective view of a preferred embodiment of the present invention illustrating a glenoid component positioned between a glenoid surface of a scapula and a humeral component.

Referring now to the drawings, FIG. 1 illustrates a glenoid component 10 of the present invention located between a left glenoid surface 12 of a scapula 14 and a humeral component 24. Glenoid component 10 is designed to be attached to glenoid surface 12 of scapula 14 to replace the natural glenoid surface 12. Glenoid component 10 includes a body portion 16 having a generally convex surface 20 for abutting glenoid surface 12. A plurality of attachment Pegs 30, 32, and 34 extend away from the convex surface 20 to anchor body portion 16 to glenoid surface 12. Body portion 16 also includes a generally concave surface 22 which provides a bearing surface for a head portion 26 of humeral component 24. Humeral component 24 also includes a stem 28 for attaching the humeral component 26 to the humerus (not shown).

The plurality of attachment pegs 30, 32, and 34 of the glenoid component 10 are configured to be inserted into a plurality of holes 13 formed in glenoid surface 12. The holes 13 for receiving attachment pegs 30, 32, and 34 are aligned along a superior/inferior axis 17 of glenoid surface 12. The glenoid surface 12 is also formed to include holes 15 for receiving first and second stabilizing pegs 40 and 42, as discussed below. The holes 15 are aligned along an anterior/posterior axis 19 of the glenoid surface 12. Holes 13 and 15 are formed in glenoid surface 12 with a suitable drilling tool (not shown). A drill guide (not shown) may be used to properly align holes 13 and 15 on glenoid surface 12.

Figure 2:
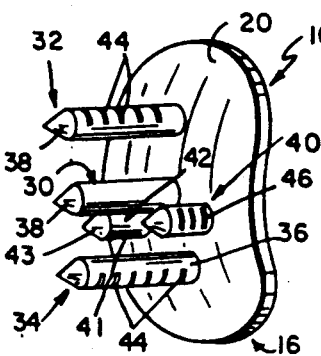
FIG. 2 is a perspective view of the glenoid component of the present invention illustrating the configuration of attachment pegs and stabilizing pegs extending away from a convex surface of the glenoid component.

As best shown in FIG. 2, glenoid component 10 includes a center attachment peg 30, a superior attachment peg 32, and an inferior attachment peg 34. Each of the attachment pegs 30, 32, and 34 include a cylindrical body portion 36 and a conical tip portion 38. Conical tip portion 38 facilitates insertion of the attachment pegs 30, 32, and 34 into the holes 13 in glenoid surface 12. The diameter of cylindrical body portion 36 is slightly less than the diameter of holes 13 formed in glenoid surface 12 to provide space for a cement mantle around the inner circumference of holes 13.

Glenoid component 10 also includes first and second stabilizing pegs 40 and 42, respectively, extending away from convex surface 20. First and second stabilizing pegs 40 and 42 each include a cylindrical body portion 41 and a conical tip portion 43 to facilitate insertion of stabilizing pegs 40 and 42 into holes 15 formed in glenoid surface 12. The diameter of cylindrical body portion 41 is slightly less than the diameter of holes 15 in glenoid surface 12.

Figure 2A:
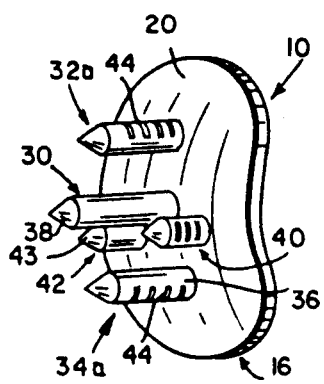
FIG. 2A is a modification of the embodiment of FIG. 2 wherein the two outer attachment pegs are made shorter in length than the center attachment peg.

In the preferred embodiment, attachment pegs 30, 32, and 34 are longer than stabilizing pegs 40 and 42 to anchor the glenoid component 10 to the bone. Attachment pegs 30, 32, and 34 are aligned along the superior/inferior axis 17 which typically has the deepest portion of bone lying under glenoid surface 12. As shown in FIG. 2A, the length of superior and inferior attachment pegs 32a and 34a may be reduced in another embodiment of the present invention when the condition of the bone underlying glenoid surface 12 requires shorter attachment pegs. The shorter stabilizing pegs 40 and 42 are used to stabilize the glenoid component 10 after attachment to glenoid surface 12. By spacing the stabilizing pegs 40 and 42 away from the superior/inferior axis 17, rocking movement of the glenoid component 10 about the superior/inferior axis 17 due to contact of bearing surface 22 with head portion 26 is prevented.

Figure 3:
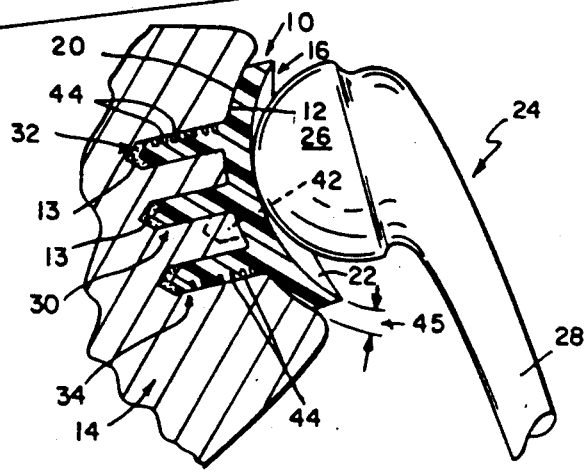
FIG. 3 is a sectional view taken along lines 3—3 of FIG. 1 illustrating the attachment pegs and stabilizing pegs of the glenoid component inserted into holes formed in the glenoid surface and the head portion of the humeral component engaging a bearing surface of the glenoid component.

FIG. 3 illustrates glenoid component 10 attached to glenoid surface 12. Attachment pegs 30, 32, and 34 are situated inside holes 13 formed in glenoid surface 12. The position of stabilizing peg 42 is shown by the dotted line in FIG. 3. A suitable bone cement is inserted into the holes 13 and 15 formed in glenoid surface 12 to secure attachment pegs 30, 32, and 34 and stabilizing pegs 40 and 42 to the bone.

Superior attachment post 32 and inferior attachment post 34 are each formed to include a plurality of notches or serrations 44. For convenience, serrations 44 are formed on a portion of superior attachment post 32 and inferior attachment post 34 facing away from center attachment post 30. The serrations 44 may, however, be formed on any portion of attachment posts 32 and 34. Serrations 44 may also be formed in center attachment post 30. Serrations 44 receive portions of the bone cement to increase the area of contact between attachment pegs 32 and 34 and the bone cement to strengthen the bond between attachment pegs 32 and 34 and the bone of glenoid surface 12. Each of the stabilizing pegs 40 and 42 are also formed to include notches or serrations 46 for receiving a portion of the bone cement to secure stabilizing pegs 40 and 42 to bone of the glenoid surface 12. As discussed above, serrations 46 strengthen the bond between stabilizing pegs 40 and 42 and the bone.

The body portion 16, attachment pegs 30, 32, 34, and stabilizing pegs 40 and 42 are integrally formed from a polymeric material such a ultra high molecular weight polyethylene (UHMWPE). Attachment pegs 30, 32, and 34 as well as stabilization pegs 40 and 42 may be cut with a suitable instrument to reduce the length of the pegs. This length reduction may be required when conditions of the glenoid surface 12 and the supporting underlying bone do not permit the full length of the pegs to be received inside holes formed in the glenoid surface 12.

FIG. 3 also illustrates the cross sectional shape of body portion 16 of glenoid component 10. Generally convex surface 20 of body portion 16 is designed to match the contour of the prepared glenoid surface 12 and abuts the generally concave glenoid surface 12 of scapula 14. Generally concave surface 22 provides a bearing surface for head portion 26 of humeral component 24. The distance between convex surface 20 and concave surface 22 is preferably as small as possible to maintain a thin body portion 16 of the glenoid component 10. The distance between convex surface 20 and concave surface 22 is illustrated by dimension 45 which is preferably less than 5 mm. The thin body portion 16 does not significantly alter the height of glenoid surface 12 when glenoid component 10 is attached to glenoid surface 12. As shown in FIG. 3, the radius of curvature of concave surface 22 is greater than the radius of curvature of head portion 26.

Figure 4:
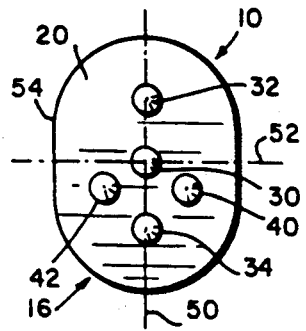
FIG. 4 is a plan view illustrating the relative spacing of the attachment pegs and the stabilizing pegs on the convex surface of the first preferred embodiment of the present invention in which the glenoid component has an oval shaped body portion.

As shown in FIG. 4, center attachment peg 30, superior attachment peg 32, and inferior attachment peg 34 are aligned with each other to lie in a single plane illustrated by line 50. First and second stabilizing pegs 40 and 42 are spaced apart from opposite sides of the attachment peg plane 50. Stabilizing pegs 40 and 42 are aligned with respect to each other to lie in a plane 52 normal to the attachment peg plane 50. Attachment peg plane 50 and stabilizing peg plane 52 intersect each other at a location in between center attachment peg 30 and inferior attachment peg 34. In the first embodiment of the present invention illustrated in FIG. 4, the body portion 16 of glenoid component 10 includes an oval shaped outer border 54.

Figure 5:
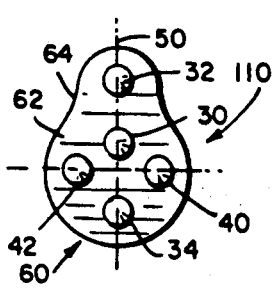
FIG. 5 is a plan view of a second preferred embodiment of the present invention illustrating glenoid component having a pear shaped body portion which includes a configuration of attachment pegs and stabilizing pegs identical to the first embodiment shown in FIG. 4.

A second preferred embodiment of the present invention is illustrated in FIG. 5. Glenoid component 110 includes a body portion 60 having a generally convex surface 62. Body portion 60 has an outer border 64 which is tear drop or pear shaped. The shape of outer border 64 more closely corresponds to a typical shape of normal glenoid surfaces 12 that have not been deformed by disease, etc. The configuration of attachment pegs 30, 32, and 34 and stabilizing pegs 40 and 42 shown in FIG. 5 is identical to the configuration of attachment pegs 30, 32, and 34 and stabilizing pegs 40 and 42 in the first embodiment shown in FIGS. 1-4. The attachment procedure for securing glenoid component 110 to glenoid surface 12 is also identical to the attachment procedure discussed above with reference to the first embodiment. It is understood that various shapes and sizes of the body portion of the glenoid component of the present invention may be selected depending upon the size and condition of glenoid surface 12 to be replaced. However, the size and configuration of attachment pegs 30, 32, and 34 and stabilizing pegs 40 and 42 will remain the same on each of the various body portions to permit easy exchangeability of the various body portions. Therefore, a single set of drilling tools can be used for installing each of the various body portions.

Additionally, the glenoid component 110 may be formed to include a buildup illustrated by dotted portion 66 in the upper posterior quadrant to abut the normal increased surface area of the upper posterior quadrant of the natural glenoid surface 12. Of course, it will be understood that the incorporation of an upper posterior quadrant buildup would require the modified components 110 to be right and left specific. However, such right and left specific components would even more closely match the natural bone surface of the glenoid surface 12. The modified component 110 shown in FIG. 5 including buildup 64 is designed for use on the left side glenoid surface 12.

Although the invention has been described in detail with reference to a preferred embodiment, variations and modifications exist within the scope and spirit of the invention as described and defined in the following claims.

What is claimed is:

1. A unitary one-piece glenoid component for attachment to a glenoid surface of a scapula to provide a bearing surface for a head portion of a humerus, the unitary one-piece glenoid component comprising a body portion having a first surface adapted to engage the glenoid surface and a second surface adapted to receive the head portion, a plurality of attachment pegs extending away from the first surface of the body portion for penetrating the glenoid surface to secure the body portion to the glenoid surface, the plurality of attachment pegs being aligned with respect to each other to lie in a single plane, and stabilizing means located on the body portion and extending in parallel to the attachment pegs to engage the glenoid surface to prevent movement of the body portion and for stabilizing the body portion when the body portion is attached to the glenoid surface.

2. The component of claim 1, wherein the stabilizing means includes a stabilizing peg extending away from the first surface for penetrating the glenoid surface to prevent movement of the body portion when the body portion is attached to the glenoid surface, the stabilizing peg being spaced apart from the attachment peg plane.

3. The component of claim 2, wherein the stabilizing peg is formed to include a plurality of serrations for receiving a bone cement to secure the stabilizing peg to the glenoid surface.

4. The component of claim 1, wherein selected attachment pegs are formed to include a plurality of serrations for receiving a bone cement to secure the selected attachment pegs to the glenoid surface.

5. The component of claim 4, wherein the plurality of attachment pegs includes a center attachment peg, a superior attachment peg, and an inferior attachment peg, the superior and inferior attachment pegs are spaced away from the center attachment peg in opposite directions, and the superior and inferior attachment pegs are formed to include the plurality of serrations.

6. The component of claim 5 wherein the center attachment peg is longer than either of the inferior or superior attachment pegs.

7. The component of claim 1, wherein the body portion is mirror symmetrical about the single plane.

8. The component of claim 1, wherein the attachment pegs include a cylindrical body portion and a conical tip portion.

9. The component of claim 1 wherein at least two of the plurality of attachment pegs have different lengths.

10. A unitary one-piece glenoid component for attachment to a glenoid surface of a scapula to provide a bearing surface for a head portion of a humerus, the unitary one-piece glenoid component comprising
a body portion having a first surface adapted to engage the glenoid surface and a second surface adapted to receive the head portion,
a plurality of attachment pegs extending away from the first surface of the body portion for penetrating the glenoid surface to secure the body portion to the glenoid surface, the plurality of attachment pegs being aligned with respect to each other to lie in a single plane, and
stabilizing means located on the body portion to engage the glenoid surface to prevent movement of the body portion for stabilizing the body portion when the body portion is attached to the glenoid surface, wherein the stabilizing means includes first and second stabilizing pegs extending away from the first surface of the body portion for penetrating the glenoid surface to prevent movement of the body portion when the body portion is attached to the glenoid surface, the first and second stabilizing pegs each being spaced apart from opposite sides of the attachment peg plane.

11. The component of claim 10, wherein the first and second stabilizing pegs are formed to include a plurality of serrations for receiving a bone cement to secure the first and second stabilizing pegs to the glenoid surface.

12. The component of claim 10, wherein the first and second stabilizing pegs include a cylindrical body portion and a conical tip portion.

13. The component of claim 10, wherein the first and second stabilizing pegs are aligned with respect to each other to lie in a plane normal to the attachment peg plane.

14. The component of claim 10, wherein the plurality of attachment pegs are aligned with a superior/inferior axis of the glenoid surface when the body portion is attached to the glenoid surface, each of the attachment pegs having a substantially equal length to extend away from the first surface by a first predetermined distance, each of the stabilizing pegs having a substantially equal length to extend away from the first surface by a second predetermined distance, the first predetermined distance being larger than the second predetermined distance so that the attachment pegs penetrate further into the glenoid surface than the stabilizing pegs when the body portion is attached to the glenoid surface.

15. A unitary one-piece glenoid component for attachment to a glenoid surface by a bone cement to provide a bearing surface for a head portion of a humerus, the unitary one-piece glenoid component comprising
a body portion including a first surface adapted to engage the glenoid surface and a second surface adapted to receive the head portion, and
a plurality of attachment pegs formed integrally with the body portion and extending away from the first surface for penetrating the glenoid surface to secure the body portion to the glenoid surface, selected ones of the plurality of attachment pegs being formed to include a plurality of notches for receiving a portion of the bone cement to secure the selected attachment pegs to the glenoid surface, wherein the plurality of attachment pegs are aligned with respect to each other to lie in a single plane, the glenoid component further comprising stabilizing means situated on the body portion to extend in parallel with the single plane for engage the glenoid surface to prevent movement of the body portion after the body portion is attached to the glenoid surface.

16. The component of claim 13, wherein the stabilizing means includes first and second stabilizing pegs extending away from the first surface spaced apart from opposite side of the attachment peg plane, the first and second stabilizing pegs penetrating the glenoid surface to prevent movement of the body portion after the body portion is attached to the glenoid surface.

17. The component of claim 16, wherein the first and second stabilizing pegs are aligned with each other to lie in a plane normal to the attachment peg plane.

18. The component of claim 16, wherein the first and second stabilizing pegs are formed to include a plurality of serrations for receiving a portion of the bone cement to secure the first and second stabilizing pegs to the glenoid surface.

19. The component of claim 14, wherein the plurality of attachment pegs include a center attachment peg, a superior attachment peg, and an inferior attachment peg extending away from the first surface, the superior and inferior attachment pegs are spaced apart in opposite directions from the center peg to lie in the attachment peg plane, and the superior and inferior attachment pegs are each formed to include the plurality of serrations.

20. The component of claim 19 wherein the center attachment peg is longer than either of the inferior or superior attachment pegs.

21. The component of claim 10, wherein the body portion is mirror symmetrical about the attachment peg plane.

22. The component of claim 15 wherein at least two of the plurality of attachment pegs have different lengths.

23. A unitary one-piece glenoid component for attachment to a glenoid surface by a bone cement to provide a bearing surface for a head portion of a humerus, the unitary one-piece glenoid component comprising a body portion including a first surface adapted to engage the glenoid surface and a second surface adapted to receive the head portion, and a plurality of attachment pegs formed integrally with the body portion and extending away from the first surface for penetrating the glenoid surface to secure the body portion to the glenoid surface, selected ones of the plurality of attachment pegs being formed to include a plurality of notches for receiving a portion of the bone cement to secure the selected attachment pegs to the glenoid surface, wherein the plurality of attachment pegs are aligned with respect to each other to lie in a single plane, the glenoid component further comprising stabilizing means situated on the body portion for engaging the glenoid surface to prevent movement of the body portion after the body portion is attached to the glenoid surface wherein the stabilizing means includes first and second stabilizing pegs extending away from the first surface spaced apart from opposite sides of the attachment peg plane, the first and second stabilizing pegs penetrating the glenoid surface to prevent movement of the body portion after the body portion is attached to the glenoid surface, wherein the plurality of attachment pegs are aligned with a superior/inferior axis of the glenoid surface when the body portion is attached to the glenoid surface, each of the attachment pegs having a substantially equal length to extend away from the first surface by a first predetermined distance, each of the stabilizing pegs having a substantially equal length to extend away from the first surface by a second predetermined distance, the first predetermined distance being larger than the second predetermined distance so that the attachment pegs penetrate further into the glenoid surface than the stabilizing pegs when the body portion is attached to the glenoid surface.

24. A unitary one-piece glenoid component for attachment to a glenoid surface of a scapula to provide a bearing surface for a head portion of a humerus, the unitary one-piece glenoid component comprising a body portion including a generally convex surface, adapted to engage the glenoid surface and a generally concave surface adapted to receive the head portion, a center attachment peg extending away from the convex surface of the body portion, a superior attachment peg and an inferior attachment peg extending away from the convex surface of the body portion spaced apart from the center peg in opposite directions, the center attachment peg, superior attachment peg, and inferior attachment peg being aligned with each other to lie in a single plane for penetrating the glenoid surface to secure the body portion to the glenoid surface, and first and second stabilizing pegs extending away from the convex surface of the body portion spaced apart from opposite sides of the attachment peg plan, the first and second stabilizing pegs penetrating the glenoid surface to prevent pivotal movement of the body portion about the attachment peg plane after the body portion is attached to the glenoid surface.

25. The component of claim 24, wherein the superior attachment peg and the inferior attachment peg are each formed to include a plurality of serrations for receiving a bone cement to secure the superior and inferior attachment pegs to the glenoid surface.

26. The component of claim 24, wherein the first and second stabilizing pegs are each formed to include a plurality of serrations for receiving a bone cement to secure the first and second stabilizing pegs to the glenoid surface.

27. The component of claim 24, wherein the first and second stabilizing pegs are aligned, with each other to lie in a plane normal to the single plane.

28. The component of claim 27, wherein the single plane and the normal plane intersect each other at a location between the center attachment peg and the inferior attachment peg.

29. The component of claim 24, wherein the body portion is mirror symmetrical about the attachment peg plane.

30. The component of claim 24, wherein the first and second stabilizing pegs are shorter than the three attachment pegs.

31. The component of claim 24, wherein the attachment pegs and the stabilizing pegs are integrally formed with the body portion.

32. The component of claim 31, wherein the body portion, the attachment pegs, and the stabilizing pegs are formed from a polymeric material.

33. The component of claim 27, wherein the center attachment peg, the superior attachment peg, and the inferior attachment peg are aligned with a superior/inferior axis of the glenoid surface when the body portion is attached to the glenoid surface, each of the attachment pegs having a substantially equal length to extend away from the convex surface by a first predetermined distance, each of the stabilizing pegs having a substantially equal length to extend away from the convex surface by a second predetermined distance the first predetermined distance being larger than the second predetermined distance so that the attachment pegs penetrate further into the glenoid surface than the stabilizing pegs when the body portion is attached to the glenoid surface.

34. The component of claim 24 wherein the center attachment peg is longer than either of the inferior or superior attachment pegs.

* * * * *

UNITED STATES PATENT AND TRADEMARK OFFICE
CERTIFICATE OF CORRECTION

PATENT NO. : 5,032,132
DATED : July 16, 1991
INVENTOR(S) : Matsen, III et al.

It is certified that error appears in the above-identified patent and that said Letters Patent is hereby corrected as shown below:

In column 5, line 33, please delete "a" and insert therefor --as--.

In column 8, line 37 (claim 16), change "13" to --15--.

In column 8, line 52 (claim 19), change "14" to --15--.

In column 8, line 63 (claim 21), change "10" to --15--.

In column 10, line 6, change "plan" to --plane--.

In column 10, line 40 (claim 33), change "27" to --24--.

Signed and Sealed this

Second Day of March, 1993

*Attest:*

STEPHEN G. KUNIN

*Attesting Officer*  *Acting Commissioner of Patents and Trademarks*